United States Patent [19]

Jones et al.

[11] Patent Number: 4,827,021

[45] Date of Patent: May 2, 1989

[54] PROCESS FOR THE PREPARATION OF ALKYL 3-ALKOXYPROPIONATES

[75] Inventors: Glenn C. Jones; William D. Nottingham; Peter W. Raynolds, all of Kingsport, Tenn.

[73] Assignee: Eastman Kodak Company, Rochester, N.Y.

[21] Appl. No.: 164,663

[22] Filed: Mar. 7, 1988

[51] Int. Cl.$^4$ .............................................. C07C 69/66
[52] U.S. Cl. ..................................... 560/187; 502/168
[58] Field of Search .......................... 560/187; 502/168

[56] References Cited

U.S. PATENT DOCUMENTS

| | | | |
|---|---|---|---|
| 2,436,286 | 2/1948 | Brooks | 260/484 |
| 2,910,503 | 10/1959 | Fox | 260/484 |
| 3,049,560 | 8/1962 | Enk et al. | 260/484 |
| 3,052,713 | 9/1962 | Jowitt | 260/484 |
| 3,134,807 | 5/1964 | Enk et al. | 560/187 |
| 4,785,133 | 11/1988 | Raynolds et al. | 560/187 |

FOREIGN PATENT DOCUMENTS

| | | | |
|---|---|---|---|
| 475852 | 8/1951 | Canada | 560/187 |
| 612378 | 1/1961 | Canada . | |
| 685185 | 4/1964 | Canada . | |
| 828371 | 2/1960 | United Kingdom | 560/187 |
| 923341 | 4/1963 | United Kingdom . | |

OTHER PUBLICATIONS

Sorm et al., *Chemical Abstracts* vol. 49, No. tt5c (1953).

*Primary Examiner*—Bruce D. Gray
*Attorney, Agent, or Firm*—J. Frederick Thomsen; William P. Heath, Jr.

[57] ABSTRACT

Disclosed is an improved process for the preparation of alkyl 3-alkoxypropionates by the reaction of a dialkoxymethane with a diketene in the presence of methanedisulfonic acid, methanetrisulfonic acid or mixture thereof.

4 Claims, No Drawings

PROCESS FOR THE PREPARATION OF ALKYL 3-ALKOXYPROPIONATES

DESCRIPTION

This invention concerns a novel process for the preparation of ether-ester compounds especially useful as solvents in the formulation of coating compositions. More particularly, this invention concerns a novel process for the preparation of alkyl 3-alkoxypropionates by the reaction of a dialkoxymethane with a ketene in the presence of certain di- and tri-sulfonic acids.

The synthesis of alkyl 3-alkoxypropionates by the reaction of a dialkoxymethane with a ketene is well known in the literature as shown by U.S. Pat. Nos. 2,436,286, 2,910,503 and 3,052,713 and Chem. Listy, 47, 413 (1953) abstracted at C.A. 49:175C. Although the cited references suggest that various proton and Lewis acids may be used to catalyze the reaction, only the use of boron trifluoride and zinc chloride have been shown to effect the formation of alkyl 3-alkoxypropionates to any significant degree. Although useful in the reaction, boron trifluoride is expensive and presents corrosion, toxicity and waste disposal problems as compared to most proton acids. Zinc chloride is a poor catalyst for the reaction and also poses disposal problems. Two other Lewis acids have been found to be unsatisfactory. Boron triacetate is inactive while the extremely active aluminum chloride gives a complex mixture of products at low conversion.

U.S. Pat. No. 2,436,286 mentions specifically the use of benzenesulfonic acid as a catalyst in the reaction of a dialkoxymethane compound with a ketene although no results are given with respect to its use. We have found that benzenesulfonic acid is esentially inactive, especially in catalyzing reactions employing diethoxymethane or higher dialkoxymethanes. Methanesulfonic acid and a sulfonic acid ion exchange resin (Amberlyst 15) were found to be similar in activity to benzenesulfonic acid. Arylpolysulfonic acids were found to have insufficient catalytic activity with 1,3- and 1,4-benzenedisulfonic acids having poor activity and 1,2-benzenedisulfonic acid and 1,3,5-benzenetrisulfonic acid having only fair activity.

We have discovered that methanedisulfonic and methanetrisulfonic acids are excellent catalyst for the preparation of alkyl 3-alkoxypropionates by the reaction of a dialkoxymethane with a ketene according to known procedures. The activity of such acidic catalysts in the manufacture of alkyl 3-alkoxypropionates is good to excellent and their use does not involve any unusual disposal or toxicity problems. Furthermore, the methanepolysulfonic acid catalysts employed in our novel process are relatively inexpensive and require no unusual handling procedures. While the methanepolysulfonic acids, as well as certain other acidic compounds referred to hereinabove, are characterized as catalysts for the reaction, they are partially consumed in the process of preparing the alkyl 3-alkoxypropionates, i.e., all catalysts acidic enough to cause a rection also react to some extent with the dialkoxymethane reactant or alcohol derived therefrom to give inactive esters or complexes. However, if desired unreacted catalyst may be recycled. For example, the distillation residue, resulting from the distillative isolation of the alkyl 3-alkoxypropionate from the crude product initially obtained from the process, may be recycled to the reactor to which the ketene and dialkoxymethane are fed.

The process of our invention involves the preparation of alkyl 3-alkoxypropionates by reacting a dialkoxymethane with a ketene in the presence of a catalytic amount of methanedisulfonic acid, methanetrisulfonic acid or a mixture thereof. The reactants and reaction conditions involved in the process of the invention are well known as shown by the references cited hereinabove. The dialkoxymethane reactant has the structure

wherein $R^1$ and $R^2$ are the same or different alkyl groups, e.g., alkyl containing up to about eight carbon atoms. Typically, $R^1$ and $R^2$ represent the same alkyl groups of up to about four carbon atoms such as methyl, ethyl, propyl, isopropyl, butyl and isobutyl. Preferably, $R^1$ and $R^2$ are both ethyl.

The ketene compounds which may be used in the process have the general formula

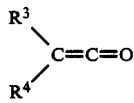

wherein $R^3$ and $R^4$ are hydrogen or the same or different substituent selected from alkyl or aryl groups. In addition to the substituents which $R^3$ and $R^4$ may represent individually, they also may represent collectively alkylene groups such as pentamethylene, hexamethylene, oxadiethylene, thiadiethylene, etc. Typical alkyl and aryl groups represented by $R^3$ and $R^4$ are methyl, ethyl, propyl, isopropyl, butyl, isobutyl, phenyl and p-tolyl. The preferred reactant is ketene, i.e., wherein each of $R^3$ and $R^4$ is hydrogen.

The temperature at which our novel process may be carried out normally should be in the range of about 10° to 50° C. Operating at temperatures outside of this range gives poor reaction rates and/or poor yields due to the conversion of the ketene to other products or decomposition of the dialkoxymethane reactant. The ratio of the reactants is not important although the process normally is performed using a stoichiometric excess of the dialkoxymethane reactant to avoid dimerization and polymerization of the ketene reactant. The ratio of the reactants present in the reactor at any given time is difficult to determine at any given time because of their reactivity. When the process is conducted in a batch manner the ketene reactant generally is added over a period of time to a mixture of the catalyst in a dialkoxymethane. The ketene addition may be continuous or semi-continuous and should be at a rate sufficient to provide an acceptable conversion of the ketene to the desired alkyl alkoxypropionate product. When performing the process in a continuous manner a stream of a dialkoxymethane containing the catalyst is combined and mixed with a stream of the ketene reactant. The mole ratio of dialkoxymethane to ketene fed to the reactor regardless of the mode of operation may be in the range of about 1:1 to 20:1 although ratios in the range of about 1:1 to about 2:1 normally are used to maximize the conversion of the dialkoxymethane and thereby avoid the disposal or recycle of it.

The methanepolysulfonic acids used as catalysts in the process provided by our invention are known materials and may be purchased or prepared according to published procedures. Methanedisulfonic acid may be prepared according to the procedures described in U.S. Pat. No. 2,842,589 and in Rec. Des. Trav. Chim. Des. Pay-Bas, 48:949 (1929). Essentially pure methanetrisulfonic acid can be obtained by heating acetic anhydride and 65% oleum and recrystallizing the crude product obtained from water as described in U.S. Pat. No. 2,333,701 (1943). Crude methanetrisulfonic acid may be obtained by heating a mixture of acetic acid with 65% oleum, also as disclosed in U.S. Pat. No. 2,333,701. The pure methanepolysulfonic acids exist as hydrates, with one water molecule for each sulfonic acid group. Purchased methanetrisulfonic acid (Custom ChemLabs, Livermore, CA) was found to contain a mixture of methanedisulfonic acid and methanetrisulfonic acid in a di:tri weight ratio of approximatey 1:2. We have found that at least some of the materials prepared according to U.S. Pat. No. 2,333,701 and characterized as methanetrisulfonic acid actually contain from minor to significant amounts of catalytically-active methanedisulfonic acid and other unidentified products.

The amount of methanepolysulfonic acid which is catalytically effective in the process provided by our invention can be varied substantially depending, for example, on the activity of the particular methanepolysulfonic acid used, the design of the reactor or reactors, the ratio of reactants, the rate and degree of conversion desired, etc. Typically, about 0.005 to 0.5 weight percent of the methanepolysulfonic acid based on the weight of the dialkoxymethane reactant will be catalytically effective with amounts in the range of about 0.01 to 0.2 weight percent being preferred. The term "catalyst" is used herein with the understanding that at least some of the catalyst is consumed during the operation of the process.

We have found that methanetrisulfonic acid, both in pure or crude form, e.g., methanetrisuflonic acid containing minor to significant amounts of methanedisulfonic acid and unknown reaction product, is especially active in catalyzing the reaction of a ketene with a dialkoxymethane to obtain an alkyl 3-alkoxypropionate. Thus, a particularly preferred embodiment of our invention comprises carrying out the process in the presence of methanetrisulfonic acid in a concentration of about 0.005 to 0.10, preferably 0.03 to 0.05, weight percent based on the weight of the dialkoxymethane reactant.

The process may be carried out in a batch, semi-continuous or continuous manner. A preferred mode of operation involves a counter-current absorber-reactor wherein the dialkoxymethane compound and catalyst are fed to the upper portion of a packed column and the ketene is fed to the lower portion. As the ketene gas contacts the mixture of dialkoxymethane and catalyst it dissolves in and reacts with the dialkoxymethane to produce the alkyl 3-alkoxypropionate product which is removed from the bottom of the column along with excess dialkoxymethane, any unreacted ketene and catalyst as well as byproducts. The column underflow may be refined directly, for example, by distillation with or without prior neutralization. If the column underflow contains a significant amount of ketene, the underflow may be fed to one or more hold-tanks to permit complete reaction of the ketene prior to purifying the crude reaction mixture.

The primary reaction which occurs during the process is represented by the equation:

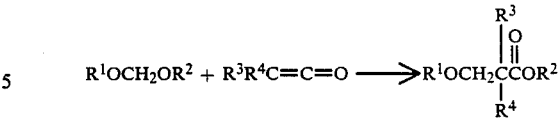

wherein $R^1$, $R^2$, $R^3$ and $R^4$ are defined hereinabove. When $R^1$ and $R^2$ represent different alkyl groups, the product will be a mixture of two or more compounds.

The process is particularly useful for the preparation of ethyl 3-ethoxypropionate by the reaction of diethoxymethane ($R^1=R^2=$ethyl) with ketene ($R^3=R^4=$hydrogen).

Our novel process is further illustrated by the following examples.

EXAMPLES 1-7

A weighed amount of dimethoxymethane (DMM, Examples 1-3) or diethoxymethane (DEM, Examples 4-7) and catalyst is placed in a magnetically-stirred, three-neck flask equipped with a thermometer, gas inlet tube above the liquid surface and a dry ice condenser. Ketene is added over the surface of the dialkoxymethane reactant with a nitrogen flow from a diketene cracking furnace. Excess ketene is used due to some being lost through the condenser. The temperature is controlled between 25° and 40° C. by the rate of ketene addition which is completed in one to two hours. When the exotherm stops, ketene addition is stopped and the reaction mixture is allowed to come to 25° C. After 30 minutes at 25° C., the reaction mixture is sampled for gas chromatography (GC) analysis. In Examples 1 and 2, 2.0 g decane are used as a GC Internal Standard.

In Example 1 the catalyst used is methanedisulfonic acid (MDSA) obtained from dichloromethane and potassium sulfite according to the procedure described in Rec. Des. Trav. Chim. Des. Pay-Bas, 48:949 (1929). The pure methanetrisulfonic acid (MTSA-R) used in Examples 2 and 5 is prepared from 65% oleum (65% free sulfur trioxide in sulfuric acid) and acetic anhydride according to the procedure disclosed in U.S. Pat. No. 2,333,701. The crude methanetrisulfonic acid obtained is purified by dissolving in a minimum amount of water and heating to 50° C., adding activated charcoal and a filtering aid and filtering. The water in the filtrate is stripped under vacuum and the recrystallized MTSA is dried in a vacuum oven at 75° C. and 20 inches Hg pressure.

The crude methanetrisulfonic acid (MTSA-C) used without purification in Examples 3 and 6 is prepared fom 65% oleum and acetic acid according to the procedure of U.S. Pat. No. 2,333,701. The methanetrisulfonic acid (MTSA-P) used in Example 7 is obtained from Custom ChemLabs. The purchased methanetrisulfonic acid consisted of a mixture of methanedisulfonic acid and methanetrisulfonic acid in a weight ratio of di-tri of approximately 1:2. The methanedisulfonic acid (MDSA-P) used in Example 4 was purchased from Kodak Laboratory Chemicals in the form of a 50% aqueous solution. The MDSA-P used was obtained by removing the water under vacuum.

The following Table shows the amounts (g) of catalyst and dialkoxymethane (DAM) reactant used, the amount (moles) of ketene added, and the amounts (g) of unreacted DAM reactant and alkyl 3-alkoxypropionate (AAP) product obtained in each of Example 1-7. In Examples 4 and 5 the DEM used has a very high purity of 99.99% DEM with 0.01% water. In the other examples the DAM reactant has a purity of approximately 99.9% with 0.1% water. MMP and EEP designate methyl 3-methoxypropionate and ethyl 3-ethoxypropionate, respectively.

TABLE

| Example | Catalyst | DAM Rectant | AAP Product | Ketene Added | Unreacted DAM |
|---------|----------|-------------|-------------|--------------|---------------|
| 1 | MDSA 0.071 | DMM 23.0 | MMP 24.9 | 0.30 | DMM 2.4 |
| 2 | MTSA-R 0.005 | DMM 23.0 | MMP 13.5 | 0.16 | DMM 10.3 |
| 3 | MTSA-C 0.012 | DMM 40.0 | MMP 38.3 | 0.46 | DMM 15.8 |
| 4 | MDSA-P 0.060 | DEM 50.0 | EEP 62.0 | 0.61 | DEM 2.9 |
| 5 | MTSA-R 0.010 | DEM 50.0 | EEP 49.7 | 0.49 | DEM 13.9 |
| 6 | MTSA-C 0.007 | DEM 42.0 | EEP 26.2 | 0.26 | DEM 21.6 |
| 7 | MTSA-P 0.020 | DEM 40.0 | EEP 43.0 | 0.42 | DEM 5.6 |

EXAMPLE 8

A. Dimethoxymethane (381 g, 5.0 mol) and pure methanetrisulfonic acid (0.148 g) are charged to a one liter, magnetically-stirred, three-neck flask equipped with a thermometer, gas inlet tube and a dry ice condenser. Ketene is added over the surface of the dimethoxymethane with a nitrogen flow from a diketene cracking furnace. The reaction mixture is cooled externally to maintain a temperature of 40° C. while adding the ketene as fast as possible. Ketene addition is terminated when the exotherm stops and a sample of the reaction mixture is analyzed by GC. The reaction mixture consisting of 87% methyl 3-methoxypropionate, 8% dimethoxymethane and 5% other compounds is vacuum distilled through a 10 plate Oldershaw column at 30 Torr and 57° C. to recover methyl 3-methoxypropionate (505 g, 4.28 mol) and unreacted dimethoxymethane (31 g, 0.4 mol).

B. Procedure A is repeated using dimethoxymethane (152 g, 2.0 mol) and the black, liquid distillation residue (13 g) resulting from Procedure A. GC analysis of the reaction mixture shows that it consists of 87.3% methyl 3-methoxypropionate, 5.8% dimethoxymethane and 6.9% other material. Vacuum distillation of the reaction mixture gives methyl 3-methoxypropionate (201 g, 1.7 mol) and dimethoxymethane (9.2 g, 0.12 mol) and a distillation residue of 20 g of black liquid. The 20 g distillation residue failed to catalyze the reaction of additional dimethoxymethane and ketene.

EXAMPLE 9

A. Example 8A is repeated using diethoxymethane (319 g, 3.06 mol) and crude methanetrisulfonic acid (0.220 g). GC analysis establishes that the resulting reaction mixture consists of 83% ethyl 3-ethoxypropionate, 9% diethoxymethane and 8% other material. Vacuum distillation of the reaction mixture at 25 Torr through a 10 plate Oldershaw column gives ethyl 3-ethoxypropionate (357.8 g, 2.45 mol) and diethoxymethane (32.5 g, 0.31 mol). The distillation residue consisted of 20 g of black liquid.

B. Example 8A is repeated using diethoxymethane (312 g, 3.0 mol) and the distillation residue of Example 9A. Vacuum distillation of the reaction mixture thus obtained gives ethyl 3-ethoxypropionate (170 g, 1.16 mol) and unreacted diethoxymethane (188 g, 1.8 mol).

While the invention has been described in detail with particular reference to preferred embodiments thereof, it will be understood that variations and modifications can be effected within the spirit and scope of the invention.

We claim:

1. Process for the preparation of an alkyl 3-alkoxypropionate which comprises reacting at a temperature of 10° to 50° C. a dialkoxymethane with a ketene in the presence of a catalytic amount of methanedisulfonic acid, methanetrisulfonic acid or mixtures thereof.

2. Process for the preparation of an alkyl 3-alkoxypropionate having the formula which comprises reacting a dialkoxymethane having the formula

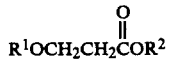

$$R^1OCH_2CH_2COR^2$$

with ketene at a temperature of 10° to 50° C. in the presence of a catalytic amount of methanetrisulfonic or a mixture of methanetrisulfonic acid and methanedisulfonic acid, wherein $R^1$ and $R^2$ each is alkyl of up to about 4 carbon atoms.

3. Process according to claim 2 wherein the process is carried out in the presence of 0.005 to 0.10 weight percent methanetrisulfonic acid or a mixture of methanetrisulfonic acid and methanedisulfonic acid based on the weight of the dialkoxymethane reactant.

4. Process for the preparation of an alkyl 3-alkoxypropionate having the formula

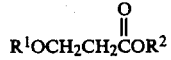

$$R^1OCH_2CH_2COR^2$$

which comprises reacting a dialkoxymethane having the formula $R^1OCH_2OR^2$ with ketene at a temperature of 10° to 50° C. in the presence of 0.01 to 0.20 weight percent, based on the weight of the dialkoxymethane, methanetrisulfonic acid; wherein each $R^1$ and $R^2$ is methyl or ethyl.

* * * * *

UNITED STATES PATENT AND TRADEMARK OFFICE
CERTIFICATE OF CORRECTION

PATENT NO. : 4,827,021
DATED : May 2, 1989
INVENTOR(S) : Glenn C. Jones, William D. Nottingham, Peter W. Raynolds It is certified that error appears in the above-identified patent and that said Letters Patent is hereby corrected as shown below:

Column 6, lines 27-34, in Claim 2, should read

---propionate having the formula $$R^1OCH_2CH_2\overset{O}{\underset{\|}{C}}OR^2$$

which comprises reacting a dialkoxymethane having the formula $$R^1OCH_2OR^2$$

with ketene at a temperature of 10° to 50°C. in the---.

Signed and Sealed this

Ninth Day of January, 1990

*Attest:*

JEFFREY M. SAMUELS

*Attesting Officer*   Acting Commissioner of Patents and Trademarks